(12) United States Patent
Somervell et al.

(10) Patent No.: US 10,124,141 B2
(45) Date of Patent: Nov. 13, 2018

(54) HUMIDIFICATION APPARATUS HAVING RFID TAG SENSOR AT PATIENT END OF GAS PATHWAY

(75) Inventors: Andrew Robert Donald Somervell, Auckland (NZ); Nordyn Alami, Auckland (NZ); Dexter Chi Lun Cheung, Auckland (NZ); Christopher Simon James Quill, Hants (NZ); Matthew Jon Payton, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 868 days.

(21) Appl. No.: 12/524,251

(22) PCT Filed: Jan. 23, 2008

(86) PCT No.: PCT/NZ2008/000007
§ 371 (c)(1),
(2), (4) Date: Mar. 22, 2010

(87) PCT Pub. No.: WO2008/091164
PCT Pub. Date: Jul. 31, 2008

(65) Prior Publication Data
US 2011/0088693 A1    Apr. 21, 2011

(30) Foreign Application Priority Data

Jan. 23, 2007    (NZ) ........................................ 552785

(51) Int. Cl.
*A61M 16/10* (2006.01)
*A61M 16/16* (2006.01)
(Continued)

(52) U.S. Cl.
CPC .... *A61M 16/1075* (2013.01); *A61M 16/0069* (2014.02); *A61M 16/109* (2014.02);
(Continued)

(58) Field of Classification Search
CPC .............. A61M 16/16; A61M 16/1075; A61M 16/0069; A61M 16/1095; A61M 16/161;
(Continued)

(56) References Cited

U.S. PATENT DOCUMENTS

| 5,558,084 A | 9/1996 | Daniell et al. |
| 6,107,611 A * | 8/2000 | Jones .................... E04D 13/103 219/213 |

(Continued)

FOREIGN PATENT DOCUMENTS

| CN | 1210020 A | 3/1999 |
| CN | 1314192 A1 | 9/2001 |

(Continued)

OTHER PUBLICATIONS

Chinese Examination Report; Application No. 200880009150.1; English Translation of partial portion of examination report; 7 pages total.

(Continued)

*Primary Examiner* — Kevin C Sirmons
*Assistant Examiner* — Leah Swanson
(74) *Attorney, Agent, or Firm* — Knobbe, Martens, Olson & Bear, LLP (57) ABSTRACT

A breathing circuit for delivering heated, humidified gases to a patient for medical purposes is described, comprising a humidifier chamber holding a quantity of water, a blower unit that delivers a pressurized gases stream to the chamber inlet, and a control system that adjusts output parameters of the breathing circuit, the circuit including a heater plate which heats the water in the chamber so that gases flowing through the chamber become heated and humidified, the circuit also including a gases transportation pathway and patient interface to convey heated humidified gases to a patient, the gases transportation pathway including an RFID (Continued)

tag located at the patient end which senses a parameter of the gases passing through the pathway, the control system including an RFID interrogator interrogating and receiving data relating to the sensed parameter from the RFID tag in real time, and adjusting the output parameters of the breathing circuit accordingly.

17 Claims, 4 Drawing Sheets

(51) Int. Cl.
  *A61M 16/06* (2006.01)
  *A61M 16/00* (2006.01)
(52) U.S. Cl.
  CPC ........ *A61M 16/1095* (2014.02); *A61M 16/16* (2013.01); *A61M 16/161* (2014.02); *A61M 16/06* (2013.01); *A61M 16/0683* (2013.01); *A61M 2016/0027* (2013.01); *A61M 2016/0033* (2013.01); *A61M 2016/1025* (2013.01); *A61M 2205/18* (2013.01); *A61M 2205/276* (2013.01); *A61M 2205/3368* (2013.01); *A61M 2205/3569* (2013.01); *A61M 2205/3592* (2013.01); *A61M 2205/581* (2013.01); *A61M 2205/583* (2013.01); *A61M 2205/6018* (2013.01); *A61M 2205/6054* (2013.01); *A61M 2210/0618* (2013.01)
(58) Field of Classification Search
  CPC .............. A61M 16/109; A61M 16/108; A61M 16/1085; A61B 5/082; A61B 5/087; A61B 5/117; A61B 5/411; G06F 19/3406; G06F 19/3481
  USPC .......... 128/203.21–20.327, 203.14; 204/433; 600/532
  See application file for complete search history.

(56) References Cited

U.S. PATENT DOCUMENTS

| | | | |
|---|---|---|---|
| 6,357,438 B1 | 3/2002 | Hansen | |
| 6,485,462 B1* | 11/2002 | Kriesel | A61M 5/14276 604/132 |
| 7,093,479 B2* | 8/2006 | Berstis et al. | 73/23.2 |
| 2002/0095980 A1* | 7/2002 | Breed | B60C 11/24 73/146 |
| 2004/0074493 A1 | 4/2004 | Seakins et al. | |
| 2004/0079370 A1* | 4/2004 | Gradon et al. | 128/203.26 |
| 2004/0100376 A1 | 5/2004 | Lye et al. | |
| 2004/0182386 A1 | 9/2004 | Meier | |
| 2004/0210151 A1 | 10/2004 | Tsukashima et al. | |
| 2005/0076906 A1* | 4/2005 | Johnson | 128/204.21 |
| 2005/0211761 A1 | 9/2005 | Anttila et al. | |
| 2005/0228238 A1 | 10/2005 | Monitzer | |
| 2005/0277873 A1* | 12/2005 | Stewart | A61M 5/14 604/93.01 |
| 2006/0125623 A1 | 6/2006 | Appelt et al. | |
| 2006/0150712 A1* | 7/2006 | Berstis | A61M 16/10 73/23.2 |
| 2006/0211936 A1 | 9/2006 | Hu et al. | |
| 2006/0250259 A1 | 11/2006 | Izumi | |
| 2006/0278222 A1 | 12/2006 | Schermeier et al. | |
| 2006/0283465 A1 | 12/2006 | Nickel et al. | |
| 2007/0068810 A1* | 3/2007 | Tsukashima et al. | 204/433 |
| 2007/0144519 A1* | 6/2007 | Henry et al. | 128/204.21 |
| 2007/0175471 A1 | 8/2007 | Schermeier et al. | |
| 2007/0265877 A1* | 11/2007 | Rice et al. | 705/2 |
| 2009/0236335 A1* | 9/2009 | Ben-Shmuel et al. | 219/710 |
| 2009/0320840 A1* | 12/2009 | Klasek et al. | 128/203.27 |
| 2010/0089394 A1* | 4/2010 | Sakurada et al. | 128/203.14 |
| 2012/0167880 A1* | 7/2012 | Jacob | 128/203.14 |
| 2013/0081618 A1* | 4/2013 | Korneff et al. | 128/203.14 |
| 2013/0087144 A1* | 4/2013 | Todd | 128/203.14 |

FOREIGN PATENT DOCUMENTS

| | | |
|---|---|---|
| CN | 1443081 A | 9/2003 |
| CN | 1700879 A | 11/2005 |
| CN | 1809397 A | 7/2006 |
| EP | 1 245 250 | 10/2002 |
| EP | 1 245 250 A2 | 10/2002 |
| EP | 1 579 884 | 9/2005 |
| EP | 1 579 884 A1 | 9/2005 |
| GB | 2 338 420 | 12/1999 |
| WO | WO 02/05879 A1 | 1/2002 |
| WO | 02/32486 | 4/2002 |
| WO | WO 02/32486 A1 | 4/2002 |
| WO | WO 03/018096 A1 | 3/2003 |
| WO | WO 2004/020031 A1 | 3/2004 |
| WO | 2007/081741 | 7/2007 |

OTHER PUBLICATIONS

Supplemental European Search Report; dated Dec. 1, 2011; 7 pages.
Australian Examination Report; dated Jun. 27, 2012; 5 pages.
Chinese Examination Report with English translations; dated Mar. 13, 2012; 9 pages.
Australian Examination Report; dated Aug. 29, 2013; 4 pages.
Australian Examination Report; dated Mar. 27, 2015; 3 pages.
Chinese Examination Report with English translations; 11 pages.
Australian Patent Examination Report No. 2; dated Jan. 5, 2016; 3 pages.
European Search Report; dated Aug. 22, 2016; 10 pages.

* cited by examiner

HUMIDIFICATION APPARATUS HAVING RFID TAG SENSOR AT PATIENT END OF GAS PATHWAY

This application is a United States National Phase filing of PCT/NZ2008/000007, having an International filing date of Jan. 23, 2008 which was published in English on Jul. 31, 2008 under International Publication Number WO 2008/091164 which claims the priority of New Zealand Patent No. 552785, filed on Jan. 23, 2007, which are hereby incorporated by reference in their entirety.

FIELD OF THE INVENTION

This invention relates a sensing system and component identification system, and particularly to a sensing and component identification system for use in a medical environment which allows parameters of therapeutic gases supplied to a patient to be measured.

SUMMARY OF PRIOR ART

A number of products are known in the art for measuring the temperature of gases being supplied to a patient as well as providing feedback to the gas humidification system. One common way of controlling humidification systems is to measure the temperature of gas at two points along the conduit used to supply gas to the patient, and using the temperature data gathered to adjust the power output accordingly. For example, a first temperature sensor is inserted adjacent to the output of the humidifier chamber and a second temperature sensor is located proximal to the patient (e.g. in or around the patient interface), both measuring temperature data and feeding this back to a central control system which is usually located in the housing of the blower unit or the humidifier unit (it should be noted that it is becoming more common for integrated units to be used—i.e. units where the humidifier chamber is rigidly connected in use to the blower unit). The type of sensor currently commonly employed for this purpose is a temperature probe such as a thermistor.

U.S. Pat. No. 5,558,084 to Fisher & Paykel Healthcare Limited describes measuring the temperature proximal to the patient using a temperature probe or transducer inserted into the inspiratory conduit. The temperature probe is interfaced to the control system via a cable which extends from the temperature probe along the external surface of the inspiratory conduit to the control system. A disadvantage of this type of temperature interface system is the dependency on the correct positioning of the temperature sensors. The correct functioning of the control system is very dependent on these sensors being correctly positioned. Incorrect placement or connection of the temperature sensors can lead to impaired performance of the entire humidification and breathing system. A further disadvantage is that gases may be supplied to the patient at a pressure/humidity combination which is inappropriate. It is well known that certain humidity levels are required of gases which are to be administered to a patient. Different humidity values are specifically suitable for different delivery interfaces. For example, patients or users receiving heated, humidified air through a face mask ('intact airway' users) have different requirements from patients or users who are receiving a gases stream through intubation delivery ('bypassed airway' users). 'Intact airway' users who use a nasal cannula have different requirements from users using a mask which covers the nose and mouth.

Some existing respiratory humidification devices include a control panel located on e.g. the blower unit, which allow users to manually make power adjustments or other adjustments. However, these adjustments often have no direct or intuitive relationship with the actual physical parameters they are intended to control. Often the manual controls indirectly and undesirably adjust the required gases outlet temperature (by adjusting the power to the humidifier chamber heater plate), or the power to a heater wire provided within the conduit connecting the humidifier to patient (by altering the current flowing through the heater wire), or both.

One of the most important parameters in humidified gases supply to a patient is the humidity of the gases. This is because insufficient gases humidity can lead very quickly to dehydration of the patient's airways. Accordingly, users have little or no idea where to position the dials to produce the desired result of optimum humidity in the supplied gases at the existing flow rate.

In their most basic form, RFID tags can be used to identify components when interrogated—the use of RFID tags to identify componentry for e.g. supply chain management is known. When used in this manner, RFID tags are preprogrammed with data identifying the item to which the tag is attached along with other details which may include supplier information, destination address or other relevant details. US 2007/0144519 describes a system where RFID tags are embedded or attached to various components in a medical breathing circuit in order to identify the individual components. The RFID tags may be either a passive or an active device and differently configured tags are attached to the particular individual items which are required to be individually identified. Information may be read from the RFID when the tag is polled by interrogation hardware such as a remote transceiver which transmits a radio frequency (RF) wave—i.e. an RF transceiver. The RF wave is received by the RFID and modulated. The modulated wave contains the tag identification code information and is transmitted back to the interrogation hardware, which receives and decodes the returning tag data and uses the information e.g. to identify and track the position of the particular item to which the tag is attached.

More sophisticated RFID tags are known, which can gather and transmit real-time data to the unit used to interrogate the RFID tag. RFID tags incorporating temperature and pressure sensors are available and are constructed on a material such as a piezo-electric crystal. The piezo-electric crystal element is a piece of piezo-electric material cut and finished to a specified geometric shape and orientation with respect to the crystallographic axes of the materials. These tags operate by converting an incoming radio wave (i.e. one that is transmitted by interrogation hardware), to a Surface Acoustic Wave (SAW) by using an inter-digital converter. The SAW propagates along the surface of the crystal at a speed dependent on temperature, pressure or even humidity of the system to which the RFID is attached. The surface acoustic wave reflects from a series of reflection features on the surface of the crystal and creates a pulse train with a period that depends on the temperature or pressure. The acoustic wave is then converted back to an RF wave and transmitted from the tag back to the transceiver. The receiving station picks up the pulse train and measures the period/frequency of the pulse train to derive e.g. the temperature. One example of an RFID tag used to measure temperature is the TELID2-T RFID tag.

It is also possible to alter the geometric shape of the piezo-electric material and/or reposition, add or remove some of the reflection features such that the pulse train will incorporate a binary code that can be used for identification purposes as well as data gathering purposes.

SUMMARY OF THE INVENTION

It is an object of the present invention to attempt to provide a patient interface which goes some way to overcoming disadvantages in the prior art or which will at least provide the industry with a useful choice.

In a first aspect the present invention consists in a breathing circuit for the delivery of heated, humidified gases to a patient for medical purposes, comprising:

a humidifier chamber adapted to hold a quantity of water and having an inlet and an outlet to allow gases to flow through said humidifier chamber, a blower unit adapted to in use deliver a stream of pressurised gases to the inlet of said humidifier chamber, a control system configured to adjust one or more output parameters of said breathing circuit, a heater plate which in use is located adjacent to said humidifier chamber and which is adapted to heat said quantity of water in said humidifier chamber so that said gases flowing through said chamber become heated and humidified, a gases transportation pathway connected to said outlet of said humidifier chamber to convey said gases flow to said patient, said gases transportation pathway including a patient interface adapted to supply said patient with said gases flow, said gases transportation pathway including an RFID tag located at or close to the patient end of said gases transportation pathway, said RFID tag adapted to sense a parameter of said gases passing through said gases transportation pathway, said control system including an RFID interrogator adapted to interrogate and receive data from at least one RFID tag in real time, said RFID interrogator receiving data relating to said sensed parameter, said control system adjusting the output parameters of said breathing circuit according to said received data.

In a second aspect the present invention consists in a breathing circuit for the delivery of heated, humidified gases to a patient for medical purposes comprising:

a humidifier chamber adapted to hold a quantity of water and having an inlet and an outlet to allow gases to flow through said humidifier chamber, a blower unit adapted to deliver a stream of pressurised gases to the inlet of said humidified chamber, a control system configured to adjust one or more output parameters of said breathing circuit, a heater plate which in use is located adjacent to said humidifier chamber and which is adapted to heat said quantity of water in said humidifier chamber so that said gases flowing through said chamber become heated and humidified, a gases transportation pathway connected to said outlet of said humidifier chamber to convey said gases flow to said patient, said gases transportation pathway including a heater wire running substantially the length of said pathway, said gases transportation pathway further including a patient interface adapted to supply said patient with said gases flow, said gases transportation pathway including an RFID tag located at or close to the patient end of said gases transportation pathway, said RFID tag adapted to sense a parameter of said gas passing through said gases transportation pathway, said control system including RFID interrogation hardware adapted to interrogate and receive data from an RFID tag in real time, said interrogation hardware receiving data relating to said sensed parameter, said RFID tag connected to said heater wire, said heater wire further adapted to act as an aerial for said RFID tag.

In a third aspect the present invention consists in a base unit for use as part of a breathing circuit which delivers heated, humidified gases to a patient for medical purposes, said breathing circuit of the type that includes a humidifier chamber adapted to hold a quantity of water and having an inlet and an outlet to allow gases to flow through said humidifier chamber, a source of pressurised gases which in use are delivered to the inlet of said humidifier chamber, and gases transportation pathway connected to said outlet of said humidifier chamber to convey said gases flow to said patient, said gases transportation pathway including a patient interface adapted to supply said patient with said gases flow, said base unit including;

a heater plate adapted to allow said humidifier chamber to in use be located on said plate, so that said heater plate heats said quantity of water in said humidifier chamber and gases flowing through said chamber become heated and humidified, a control system configured to adjust one or more output parameters of said breathing circuit, said control system including an RFID interrogator adapted to interrogate and receive data from at least one RFID tag in real time, said RFID interrogator receiving data relating to said sensed parameter, said control system adjusting the output parameters of said breathing circuit according to said received data.

In a fourth aspect the present invention consists in a gases conduit for use as part of a breathing circuit which delivers heated, humidified gases to a patient for medical purposes, said breathing conduit having a first end adapted for connection to the outlet of a humidifier chamber, and a second, patient end, said gases conduit including and RFID tag located at or close to said patient end, said RFID tag adapted to sense a parameter of said gases passing through said gases transportation pathway, In a fifth aspect the present invention consists in a patient interface for use as part of a breathing circuit which delivers heated, humidified gases to a patient for medical purposes, said patient interface adapted for connection to one end of a gases conduit so that heated humidified gases can be passed through said conduit and delivered to a patient via said patient interface, said patient interface including an RFID tag adapted to sense a parameter of said gases passing through said patent interface.

The invention consists in the foregoing and also envisages instructions of which the following gives example.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

The term 'comprising' as used in this specification means 'consisting at least in part of' that is to say when interpreting statements in this specification which include that term, the features, prefaced by that term in each statement, all need to be present but other features can also be present.

BRIEF DESCRIPTION OF THE DRAWINGS

Preferred forms of the present invention will now be described with reference to the accompanying drawings and which.

DETAILED DESCRIPTION OF THE PREFERRED EMBODIMENTS

A breathing circuit for the delivery of heated, humidified gases to a patient or other user requiring heated humidified gases at a pressure above atmospheric is described below. The breathing circuit incorporates a sensing mechanism by which system parameters such as temperature, pressure, gases flow rate, humidity and gas composition can be measured at or close to the point at which the gases are delivered to a patient or user using the system. The preferred form of the sensing mechanism is lightweight and small in size, and is therefore very suitable for use at the patient end of a breathing circuit, where additional weight and bulk can add to patient discomfort and increase the chances of non-compliance with a treatment regime. In the most preferred form described below, the sensing mechanism also serves to identify the individual component of the breathing circuit in which it is embedded or attached. The invention as described is suitable for both RH and OSA, and can be used with a CPAP blower unit, or a blower unit which provides other types of output profiles, such as BiPAP, variable flow and pressure, or similar.

Figure 1:
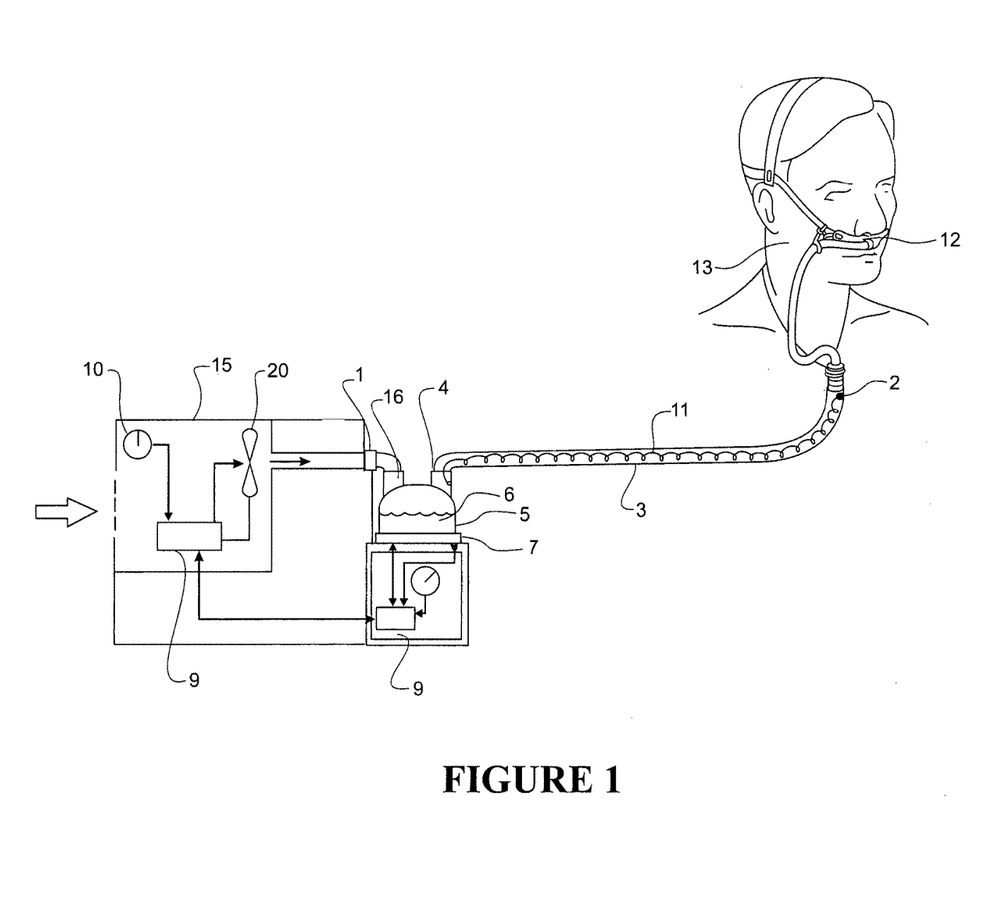
FIG. 1 shows a schematic diagram of a respiratory humidification system incorporating a radio frequency identification (RFID) tag at the patient end a breathing conduit.

An example breathing circuit apparatus or respiratory humidification system that may incorporate the sensing system and temperature sensing mechanism of the present invention is illustrated in FIG. 1. A ventilator or blower unit 15 is shown. The blower unit 15 supplies a flow of gases at a pressure above atmospheric through blower unit outlet 1. In the most preferred form, the blower unit includes a fan 20, the speed of which can be varied in order to vary the delivered pressure or flow. The gases supplied can be for example oxygen, anaesthetic gases or air. A humidifier chamber 5 is located downstream from the blower unit 15 (i.e. the humidifier chamber 5 receives gases from the blower unit 15). The humidifier unit 5 has a humidifier chamber inlet 16 which in use is fluidically connected to the blower unit outlet 1 so that gases from the blower unit 15 are delivered to the humidifier chamber 5 via the inlet 16. In the preferred embodiment, the humidifier chamber 5 has a hollow plastic body and a metal base 7. The chamber 5 is sealed apart from the humidifier chamber inlet 16 and a humidifier chamber outlet 4. The humidifier chamber 5 in use holds a volume of water 6 that in use is heated by a heater plate 7. In the preferred embodiment the heater plate 7 is included as an integral part of the blower unit 15, and the humidifier chamber 5 in use is rigidly connected to the blower unit 15 so that the blower unit 15 and the humidifier chamber 5 form an integrated blower/humidifier unit.

The preferred embodiment of the blower unit 15 also includes an integral control system, control system or control mechanism 9, which includes control circuitry that can alter the output parameters of the breathing circuit. The functionality of the control mechanism 9 will be described in more detail below. It should be noted that the control system 9 could also be located in e.g. a humidifier heater base unit, for example if the breathing circuit is of the modular type where the blower and the humidifier unit are separate (i.e. the humidifier chamber 5 is located on a heater base unit that is separate to the blower unit). In this modular type of breathing circuit, the blower outlet and the humidifier inlet would be connected in use by a length of sub-conduit. Where it would be appropriate to do so, this length of sub-conduit should be read as being part of the blower unit 15.

In use, as the water volume 6 within chamber 5 is heated, evaporation takes place, and water vapour mixes with the gases flowing through the humidifier chamber 5. Accordingly, the gases exiting the chamber 5 via the humidifier chamber outlet 4 are heated and humidified. The heated, humidified gases are passed to a patient or user 13 via a gases transportation pathway, breathing conduit or inspiratory conduit 3, which is fluidically connected to the outlet 4. In order to reduce condensation within the inspiratory conduit 3 and in order to maintain the temperature of the gases provided to the patient 13 a heater wire 11 or other suitable heating mechanism is provided. In the preferred embodiment, heater wire 11 is helically wound in or around the conduit 3 (the heater wire 11 could also be aligned straight along the conduit 3). It is further preferred that the heater wire 11 is helically or spirally wound inside the conduit 3, against the walls of the conduit 3.

A patient interface 12 is also shown in FIG. 1. The patient interface 12 is fluidically connected to the patient end of the conduit 3 so that the heated humidified gases passing along the conduit 3 from the humidifier chamber 5 can be supplied to the user 13 via the patient interface 12. It should be noted that the patient interface 12 and the conduit 3 of the preferred embodiment together form the gases transportation pathway between the humidifier chamber 5 and the patient 13. In this specification, if it would be appropriate to do so, the patient interface 12 should be read as a part of the gases transportation pathway—i.e. the patient interface 12 and the breathing conduit 3 together form the gases transportation pathway. In the preferred embodiment, the patient interface 12 is a nasal cannula fluidically connected to one end of the conduit 3 and supplying gas to the patient's nares. It should be understood that many alternative gases delivery configurations exist. For example, the patient could be intubated with a gases delivery tube positioned in the patient's trachea through a tracheostomy fitting, in order to by-pass the patient's airways. The 'patient interface' in this case would be the tube and fitting, with the conduit 3 connected to the fitting in use. Alternatively, gases could be supplied by way of e.g. a nasal mask, a full face mask, or an oral mask. The invention as conceived would work equally well with any alternative patient delivery mechanism known in the art and should not be read as being limited to the nasal cannula of the preferred form described herein. Furthermore, it should be noted that in some alternative embodiments it may be desirable to provide a return path for the patient's exhaled gases back to blower or ventilator 15 (or to atmosphere) by including a suitable fitting such as a "Y-piece" at the patient end of the delivery conduit 3, and fitting a separate return conduit or expiratory conduit (not shown).

The control mechanism, control system or control system 9 of the preferred embodiment is a microprocessor or logic circuit, which includes an associated memory or storage mechanism that holds software programs. The control circuitry 9 is also adapted so that it can receive and process real-time data gathered by sensors located at various positions in the patient breathing circuit. The control circuit 9 in the most preferred embodiment also includes manual user-operated controls. When the breathing circuit is activated by the control system 9 the breathing circuit operates in accordance with instructions included in the embedded hardware and pre-programmed software, altering the output parameters of the hardware in the breathing circuit—for example, altering the speed of the fan 20 included in the blower unit 15 in order to alter the pressure or flow in the system, altering the power to the heater plate 7 in order to alter the heat or humidity of the gases exiting the humidifier chamber, and altering the power to the heater wire 11 in order to alter the heat or humidity of the gases delivered to the patient 13. In the most preferred embodiment, the control system 9 also alters its outputs in response to the received real-time external data inputs from sensors in the breathing circuit, in accordance with pre-programmed instructions in the hardware/software of the control system 9. For example, the heater plate 7 may include a plate temperature sensor (not shown) connected to the control system 9 so that the control system 9 is provided with information on the temperature and/or power usage of the heater plate 7. Control system 9 receives the data from the sensor, and compares this with values held in its memory (e.g. in 'look-up' tables). The control system 9 can then adjust the output parameters of the heater plate 7 (e.g. the power to the heater plate) accordingly. This will be described in greater detail below. In addition, the control system 9 may be provided with gases temperature data from sensors in the system. For example, a temperature sensor may be included at the humidifier chamber outlet 4 to measure the temperature of the gases leaving the humidifier chamber 5. Both the plate temperature sensor and the humidifier chamber outlet sensor are included as part of the integrated blower/humidifier unit in the preferred embodiment, and therefore their weight is not carried by a user of the system in use. Because the weight of these temperature sensors is not carried by the patient in use, they can be of any suitable type, such as thermistors, and can be hard-wired into the control circuitry 9.

In the preferred form, some or all of the components of the breathing circuit (i.e. the blower unit 15, the humidifier chamber 5, the conduit 3 and the interface 12) also include an embedded RFID tag or tags.

Figure 2:
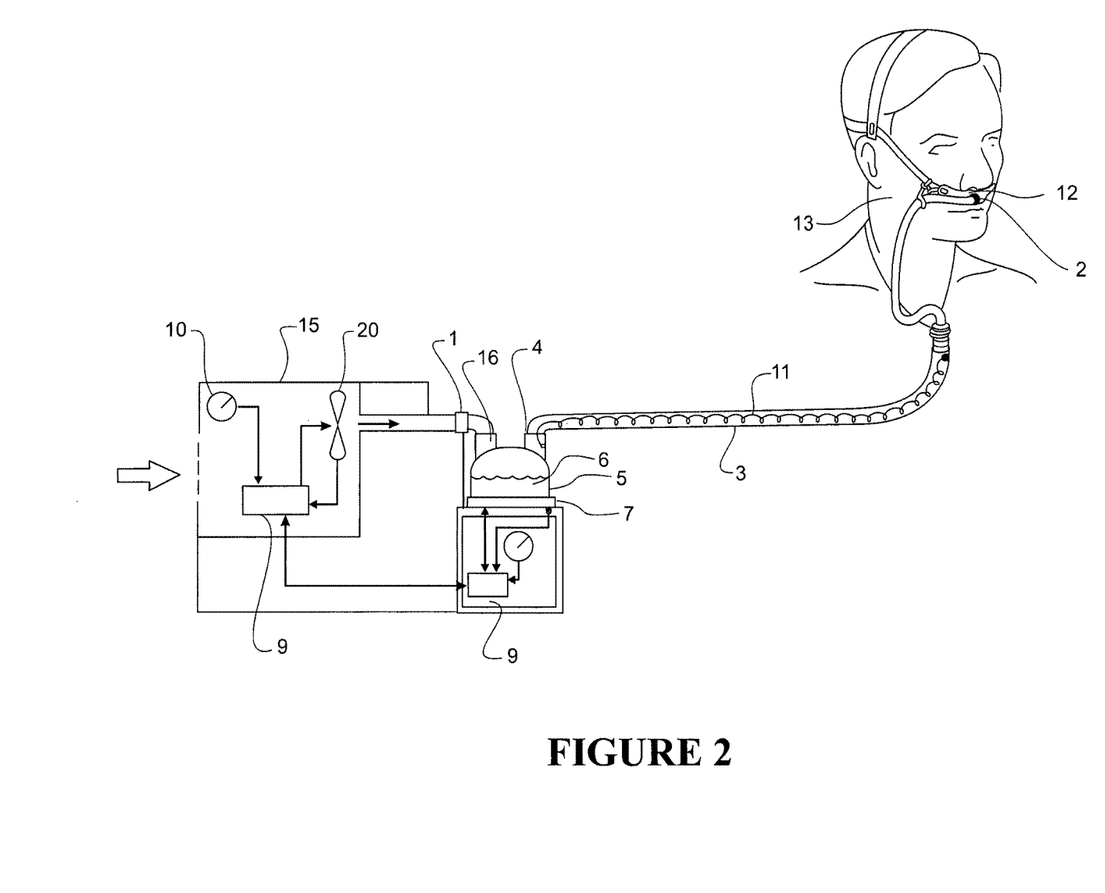
FIG. 2 shows a schematic diagram of a respiratory humidification system incorporating a radio frequency identification (RFID) tag located in a patient interface that forms part of the breathing circuit.

In their most basic form, the embedded RFID tags can be used to identify individual components of the breathing circuit when interrogated. However, in the most preferred form, at least one of the RFID tags included in the breathing circuit is also adapted to measure a parameter of the gases flowing through the system. In one preferred embodiment as shown in FIG. 1, an RFID tag 2 is located at the patient end of the breathing conduit 3, where the conduit 3 meets a smaller hose that forms part of the patient interface 12. However, it is generally preferred that the RFID tag 2 is located as close to the point at which the gases are delivered to the patient as possible, in order to measure a parameter or parameters of the gases as close to the point of delivery to the patient as possible. The RFID tag 2 in FIG. 2 is shown located in the patient interface 12.

In one preferred embodiment, the RFID tag 2 is adapted to act both as a patient identifier and also as a temperature sensor. More details of this form of RFID tag 2 will be described further below.

The control circuitry 9 of the blower unit 15 includes integral RFID interrogation hardware—i.e. an RF transceiver adapted to act as an RFID interrogator—which interrogates and receives data from RFID tags such as RFID tag 2 located in the breathing circuit. The RFID interrogation hardware and software is included as part of the blower control circuitry 9. The RFID interrogation hardware interrogates the RFID tags such as tag 2 in the breathing circuit. The information received from the RFID tags such as tag 2 is fed back to the control circuitry hardware and software 9. The control circuitry 9 then adjusts the output parameters according to its pre-programming—for example, increasing or decreasing the power output of the heater plate 7, increasing or decreasing the flow or pressure by increasing or decreasing the fan speed, and increasing or decreasing the power output of the heater wire 11.

In one preferred form, RFID tag 2 is adapted or configured to measure the temperature of the gases flowing past it. When it is located in the patient interface 12 as shown in the embodiment of FIG. 2, it is located as close as possible to the delivery point where the heated and humidified gases are delivered to the patient. Therefore, the measured temperature is at or very close to the temperature at which the gases are delivered to the patient. If the measured gases temperature is not optimal, the control circuitry 9 is programmed to adjust the power to the heater plate 7 or the heater wire 11, or both, accordingly.

RFID tag 2 as described above for one preferred embodiment is configured as a temperature sensor. It should be noted that it is possible to configure e.g. RFID tag 2 to act a pressure sensor, a humidity sensor, a flow sensor or a gases composition sensor.

Figure 3:
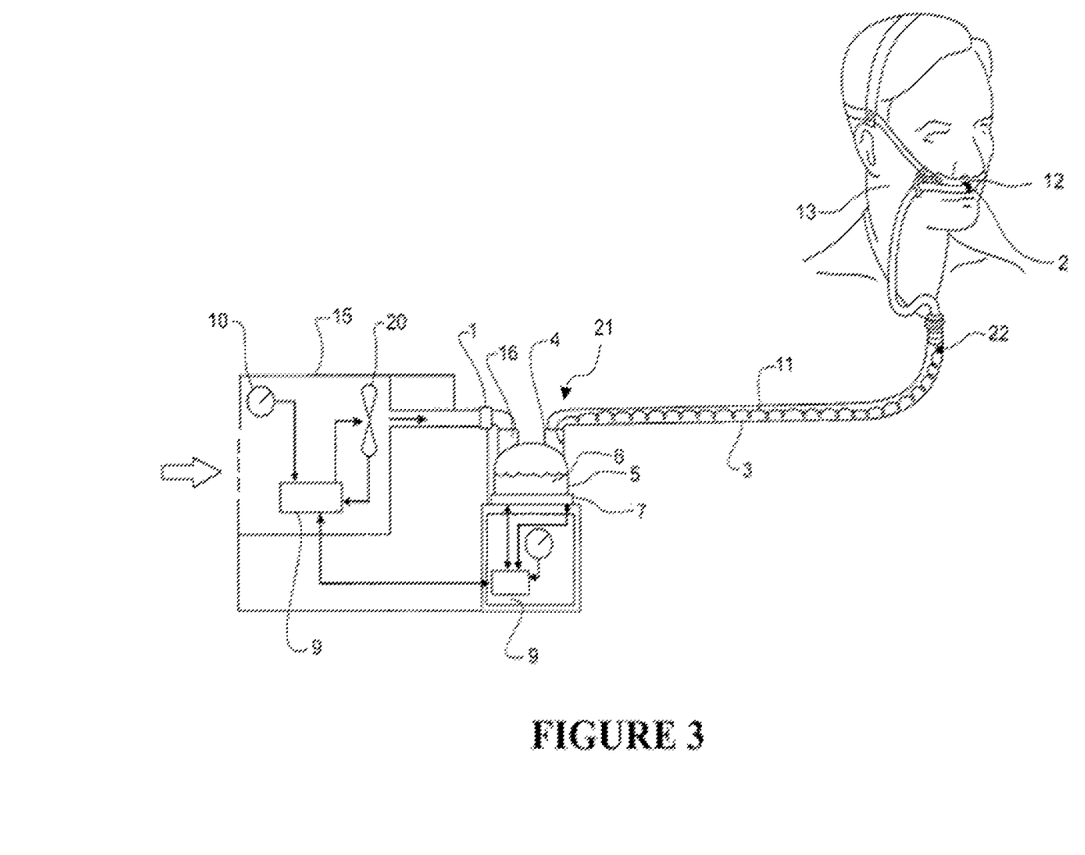
FIG. 3 shows a schematic diagram of a respiratory humidification system incorporating multiple radio frequency identification (RFID) tags located at the end of the breathing conduit, in the patient interface, and at the exit of the humidifier chamber.

RFID tags can also be located at multiple locations in the breathing circuit. For example, RFID tags could be located at the humidifier chamber outlet 4, the patient end of the conduit 3, and in the patient interface 12. These tags can be configured as temperature sensors, or some other form of sensor as outlined above. The interrogation hardware and control system 9 received data from the tags and adjust the output parameters of the breathing circuit accordingly. An example of an embodiment of the breathing circuit which contains multiple RFID tags is shown in FIG. 3. As well as RFID tag 2 located in the interface 12, the breathing circuit also includes an RFID tag 21 located at the humidifier end of the conduit 3 and an RFID tag 22 located at the patient end of the conduit 3. In this preferred form, the tags 2, 21 and 22 are configured as temperature sensors, and additionally tag 2 and one of tags 21 or 22 is configured as an identification tag. It should be noted that these additional tags could be other-wise configured to measure other parameters, or they could be placed at other locations in the breathing circuit as required.

One problem that has been discovered with using RFID tags such as tag 2 to measure temperature is that it can be difficult to interrogate the tags in real-time over longer distances. RFID tags of the passive type are intended to be used or read over very short distances, in the region of 10 cm, for example. Patient conduits are of standard lengths (e.g. six feet) and blower/humidifier units such as blower unit 15 and chamber 5 are usually located several feet away from a patient (and patient interface) in use. Because the RFID interrogation hardware is therefore usually located several feet away from e.g. RFID tag 2, it can be difficult for the interrogation hardware to receive a consistent and strong data signal, especially if RFID tag 2 is of the passive type and does not include an integral battery or an integral aerial.

Active or semi-passive RFID tags which include batteries or aerials can be reliably read over longer distances, but RFID tags of this type are usually larger in size than passive tags and are correspondingly heavier and builder. It is desirable to keep the weight of components in the breathing circuit as light as possible, especially at the patient end, so that a patient does not have to carry additional weight or bulk.

Therefore, in a second preferred form, the patient interface 12 is used with a breathing conduit that includes the heater wire 11. The RFID tag 2 (in the preferred form embedded or attached to the patient interface 12) is in use connected to the heater wire 11. The RFID tag 2 could also be included at the patient end of a stand-alone conduit. The heater wire 11 of the conduit 3 is in this embodiment adapted so that it has dual functionality: it acts as a heater wire, and also as an aerial for the RFID tag 2. The use of the heater wire 11 as an aerial greatly extends the range of data transmission. Also, one end of the heater wire 11 is located at the blower end of the breathing conduit 3, considerably closer to the blower unit 15 than the patient interface 12. Therefore the necessary transmission range is considerably shorter than would otherwise be the case. Using the heater wire 11 as an aerial allows the interrogation hardware located in the housing of the blower unit 15 to interrogate the RFID tag 2 over longer distances—for example 6 feet or more—in real time, without the RFID tag 2 requiring a battery or its own aerial. If a battery or other integral power supply is used, it does not need to be as powerful, and can therefore be smaller than would otherwise be the case. The real time temperature data gathered by the RFID tag 2 is fed back to the control circuitry 9 via the RFID interrogation hardware contained in the housing of the blower unit 15.

A semi-passive or an active tag may be required at the patient interface in some applications—e.g. RFID tag 2 may be required to be of the semi-passive or active type. In these alternative embodiments, the heater wire 11 can be further adapted so that it supplies power to the RFID tag 2 as well as acting as a heater wire in the conduit 3.

It should also be noted that the blower unit 15 can include manual user controls as well as the automatic adjustment mechanisms described above, where the power output adjustments are made by means of feedback from sensors (e.g. RFID tag 2) located at various points in the system. For example, the manual controls can include a user input mechanism such as a switch 10. Switch 10 is adapted to allow a user (such as a healthcare professional or the patient themselves) to manually set a desired gases temperature of the gases to be delivered. Alternatively or as well as having manual controls to adjust or set the temperature, the controls could include a manual adjustment of the desired gases humidity level. In some embodiment, other functions could also be manually controlled, or alternatively a user or healthcare professional could be given a choice of a number of automatic gases delivery configurations, the user choosing an individual configuration by selecting from a menu or setting the appropriate control.

As described above, the preferred form of RFID tag 2 is configured to act both as a temperature sensor and as a component identifier. It is also possible to use an RFID tag that is adapted to measure one of a number of other parameters. For example, instead of using an RFID tag that is configured to measure temperature, an RFID tag that is configured to measure pressure, or gases flow rate, or gases humidity, or gases content (i.e. oxygen percentage) could be used instead or as well as the RFID tag 2.

As outlined above, as well as being used to sense the temperature (or other parameter) of humidified gases being supplied to a patient, the RFID tag 2 may be used as a patient interface identifier, providing an identification input signal to the control system. The identification signal identifies which type of patient interface (or breathing conduit) has been connected to the blower unit (which contains the interrogation hardware). In some embodiments, the conduit 3 will include a tag at both the humidifier end and at the patient end. In this case, it is preferred that the tag at the humidifier end carries the identification data—data relating to the identity of the component or the component identity. However, the component identification data can be carried by any component tag.

In the preferred embodiment, the control system contained in the casing of the blower unit is configured to automatically change the output settings in response to the identifier signal received from the RFID tag. In one preferred form, a number of different "identification profiles" are stored in the memory of the control system 9, each one based around a predetermined required gas temperature and humidity value. Each of these profiles corresponds to an RFID identification code for tags embedded in different types of patient interface. When the blower unit 15 is switched on, the transceiver or interrogation hardware polls continuously until it receives an identification code from the RFID tag 2. The returning identification code tag data information is compared to the stored "identification profiles" and the control system automatically sets the humidifier gas temperature and humidity output levels. In the preferred forms, this humidification control system can be overridden by a user manually adjusting a switch input. However, it is preferable that humidifier autonomy is maintained to provide the most effective system operation. The advantage of this system over other systems known in the art is that user error is eliminated. The setting of the user operational mode is not dependent on user input.

In some embodiments, the RFID tags embedded in components such as the conduit 3 can carry component expiry date data. The control system 9 reads the RFID tag and compares the present date with the expiry date. If the expiry date has passed, the control system 9 can alert the user by means of an audio or visual alarm, or refuse to activate the system, or similar.

In the preferred form RFID tag 2 is constructed on a piezo-electric crystal element. The RFID tag 2 is preferably located on or within the patient interface 12 or heated inspiratory conduit 3, in close proximity to the patient 13. The piezo-electric element geometric shape is configured prior to use so that when it is interrogated, it provides a means of identifying the type of patient interface to which the RFID is being attached, and also acts as a sensor—e.g. a temperature sensor, a pressure sensor, etc). The preferred type of RFID tag and means of interrogation is by using surface acoustic wave (SAW) technology, where the properties of the returning wave will differ from the transmitted wave, and can therefore be used to measure temperature, pressure, flow, gas composition, etc. as detailed below.

With the RFID tag 2 located within the patient interface 12 or inspiratory conduit 3 and in close proximity to the patient, the piezo-electric crystal elements provide a means of sensing gas parameters (such as temperature) at the point of delivery to the patient 13. The interrogation hardware polls the RFID 2 at predetermined intervals of time. In some embodiments, the RFID tag can be energised by this incoming radio wave from the interrogation hardware. A pulse train passes across the surface of the crystal and a modulated pulse train is returned to the interrogation hardware in control system 9. A transceiver in the interrogation hardware decodes the pulse train and uses a lookup table located in the memory of control system 9 to determine the appropriate gas parameter (e.g. temperature). The parameter retrieved from the lookup table is compared with the required parameter value (e.g. temperature) for the current configuration. For example, the measured temperature is compared with the "identification profile" for the particular patient interface and the particular treatment regime specified. If there is a difference in the two values, then a control signal is generated by the control system, and the output parameters of the breathing circuit are adjusted accordingly. For example, if the RFID tag 2 is configured to measure the temperature, and the measured temperature is too low in comparison to the retrieved lookup value, the control system increases the power to the heater plate, so that the heated, humidified gases leaving the humidifier are at a higher temperature.

It should be noted that the main form of RFID tags described above are the passive type. Semi-passive or active RFID tags can also be used if required. If an active-type RFID tag is used, it does not have to be powered by using the heater wire, it can be provided with its own power source such as a battery. The RFID tag such as tag 2 could also be a microprocessor device, and could include a wireless transmitter and receiver, with (if required) its own power supply. For example, the RFID tag 2 could be replaced with a Bluetooth-type device, or any other active type of transmitter which uses wireless communication. If it would be appropriate to do so, the phrase "RFID tag" should be read broadly enough to cover these types of devices. However, passive RFID tags are the preferred form.

Figure 4:
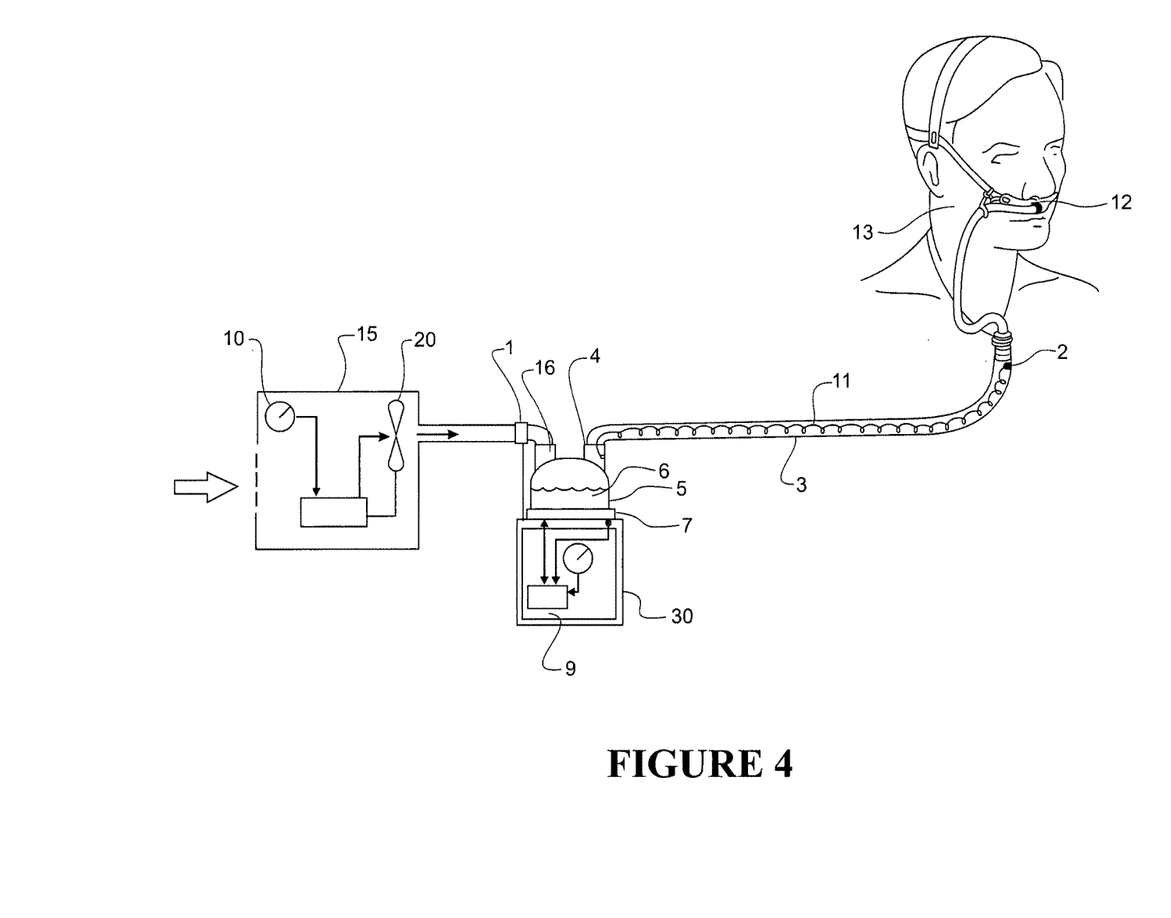
FIG. 4 shows a schematic diagram of a respiratory humidification system, which is of the modular type with a separate humidifier base unit and blower unit, a radio frequency identification (RFID) tag located in the gases conduit at the patient end.

In the preferred embodiment described above, the RFID interrogator and the control system 9 are located inside the housing of the blower unit 15. In alternative embodiments, it may be preferred to use modular components, for example a separate blower and humidifier unit, with the outlet of the blower unit and the inlet of the humidifier chamber connected in use by a separate conduit so that the gases stream from the blower unit can be delivered to the humidifier chamber. In these alternative embodiments, the humidifier part of the breathing circuit includes a base unit 30, which the humidifier chamber 5 locates onto in use, the base unit including a heater plate which heats the contents of the humidifier chamber 5. The control system 9 and the RFID interrogator can be located either in the base unit 30 or (if a blower unit is used to form the breathing circuit), in the blower unit, as required. Also, in alternate forms, the base unit can be used in a hospital which includes built-in gas supply conduits or gas sources. These are usually located in the hospital walls. The base unit 30 in these situations would contain the RFID interrogator and control system 9. A conduit would connect the hospital gases supply to the inlet of the humidifier chamber. The hospital gases supply would act as a source of pressurised gases.

It should also be noted that breathing conduits or gases conduits can be formed and sold separately for use as a part of a breathing circuit which delivers heated, humidified gases to a patient for medical purposes. The breathing conduits would have a first end adapted for connection to the outlet of a humidifier chamber, and a second, patient end, which would include an RFID tag, the RFID tag adapted to sense a parameter of the gases passing through said gases transportation pathway, in a similar manner to that described above.

The invention claimed is:

1. A breathing circuit apparatus for the delivery of heated, humidified gases to a patient for medical purposes, comprising:
    a humidifier chamber adapted to hold a quantity of water and having an inlet and an outlet to allow gases to flow through said humidifier chamber,
    a blower unit adapted to in use deliver a stream of pressurised gases to the inlet of said humidifier chamber,
    a control system configured to adjust one or more output parameters of said breathing circuit,
    a heater plate which in use is located adjacent to said humidifier chamber and which is adapted to heat said quantity of water in said humidifier chamber so that said gases flowing through said chamber become heated and humidified,
    a gases transportation pathway connected to said outlet of said humidifier chamber to convey said gases flow to said patient, said gases transportation pathway having a patient interface adapted to supply said patient with said gases flow, said gases transportation pathway having an RFID tag located at or close to a patient end of said gases transportation pathway, said RFID tag adapted to sense a parameter of said gases passing through said gases transportation pathway,
    wherein said gases transportation pathway comprises a breathing conduit with an integral heater wire, said heater wire configured to provide heat to the breathing conduit and also to act as an aerial for said RFID tag,
    and wherein said RFID tag is configured to act as a breathing circuit component identifier, said control system having an RFID interrogator adapted to interrogate and receive data from at least one RFID tag in real time, said RFID interrogator receiving data relating to said sensed parameter and said breathing circuit component identifier, said control system adjusting the output parameters of said breathing circuit according to said received data.

2. The breathing circuit apparatus as claimed in claim 1 wherein said output parameters adjusted by said control system are any combination of blower unit fan speed, heater plate power output, or a breathing circuit heater wire power output.

3. The breathing circuit apparatus as claimed in claim 1 wherein said RFID tag is also configured to act as a patient interface identifier.

4. The breathing circuit apparatus as claimed in claim 3 wherein said patient interface is one of a nasal cannula, a nasal mask, a full face mask, or a tracheostomy fitting.

5. The breathing circuit apparatus as claimed in claim 4 wherein said control system has a number of pre-set identification profiles, said RFID interrogator interrogating said RFID tag and receiving an identification code from said RFID tag, said control system automatically adjusting said output parameters based on a pre-set identification profile corresponding to said identification code.

6. The breathing circuit apparatus as claimed in claim 5 wherein at least one RFID tag in each component of said breathing circuit contains data relating to an expiry date for that component, said control system in use interrogating said RFID tag and comparing the present date to said expiry date and initiating an alarm condition if said expiry date has passed.

7. The breathing circuit apparatus as claimed in any one of claims 2 and 3-6 wherein said RFID tag is of a semi-passive or active type, and said integral heater wire is configured to provide power to said RFID tag.

8. The breathing circuit apparatus as claimed in claim 7 wherein said blower unit also has user-operable control adapted to allow a user to set output parameters of said breathing circuit.

9. The breathing circuit apparatus as claimed in claim 8 wherein said user-set output parameters are one or both of gases temperature and gases humidity.

10. The breathing circuit apparatus as claimed in any one of claims 1, 2, and 3-6 wherein said RFID tag is of a semi-passive or active type, and has an integral power supply.

11. The breathing circuit apparatus as claimed in claim 10 wherein said blower unit also has user-operable control adapted to allow a user to set output parameters of said breathing circuit.

12. The breathing circuit apparatus as claimed in claim 11 wherein said user-set output parameters are one or both of gases temperature and gases humidity.

13. The breathing circuit apparatus as claimed in claim 1 wherein said RFID tag is configured to act as a gases temperature sensor and is positioned in said patient interface to sense a temperature of gases passing through said patient interface.

14. The breathing circuit apparatus as claimed in claim 1 wherein said RFID tag is configured to act as a gases pressure sensor and is positioned in said patient interface to sense a pressure of gases passing through said patient interface.

15. The breathing circuit apparatus as claimed in claim 1 wherein said RFID tag is configured to act as a gases flow sensor and is positioned in said patient interface to measure a flow rate of gases passing through said patient interface.

16. The breathing circuit apparatus as claimed in claim 1 wherein said RFID tag is positioned in said interface and is configured to measure an oxygen content of gases passing through said patient interface.

17. The breathing circuit apparatus as claimed in claim 1 wherein said RFID tag is positioned in said patient interface and is configured to measure a humidity of gases passing through said patient interface.

* * * * *

UNITED STATES PATENT AND TRADEMARK OFFICE
CERTIFICATE OF CORRECTION

PATENT NO.       : 10,124,141 B2
APPLICATION NO.  : 12/524251
DATED            : November 13, 2018
INVENTOR(S)      : Andrew Robert Donald Somervell et al.

Page 1 of 1

It is certified that error appears in the above-identified patent and that said Letters Patent is hereby corrected as shown below:

In the Specification

In Column 4 at Line 58, change "of'" to --of',--.

In Column 9 at Line 7, change "builder." to --bulkier.--.

Signed and Sealed this
Sixteenth Day of April, 2019

Andrei Iancu
*Director of the United States Patent and Trademark Office*